(12) United States Patent
Isaac et al.

(10) Patent No.: US 11,298,260 B2
(45) Date of Patent: Apr. 12, 2022

(54) PERINEAL THERMAL PACK WITH IMPROVED LIQUID CONTAINMENT

(71) Applicant: ALLEGIANCE CORPORATION, Waukegan, IL (US)

(72) Inventors: Walter H Isaac, Lindenhurst, IL (US); Varsha Kalyankar, Kenosha, WI (US); Nichole L Wilhelm, Columbus, OH (US); Andrew T Nikolai, Chicago, IL (US); Hallie M Schmidt, Highland Park, IL (US); Taylor Marohl, Green Bay, WI (US); Aaron Dederich, Menomonee Falls, WI (US)

(73) Assignee: ALLEGIANCE CORPORATION, Chicago, IL (US)

( * ) Notice: Subject to any disclaimer, the term of this patent is extended or adjusted under 35 U.S.C. 154(b) by 785 days.

(21) Appl. No.: 15/654,459

(22) Filed: Jul. 19, 2017

(65) Prior Publication Data
US 2018/0021168 A1    Jan. 25, 2018

Related U.S. Application Data

(60) Provisional application No. 62/364,092, filed on Jul. 19, 2016.

(51) Int. Cl.
*A61F 7/02* (2006.01)
*A61F 7/00* (2006.01)
(Continued)

(52) U.S. Cl.
CPC .......... *A61F 7/02* (2013.01); *A61F 7/00* (2013.01); *A61F 7/10* (2013.01);
(Continued)

(58) Field of Classification Search
CPC ...... A61F 7/02; A61F 7/00; A61F 7/10; A61F 13/47236; A61F 13/51305; A61F 13/539;
(Continued)

(56) References Cited

U.S. PATENT DOCUMENTS

| | | | |
|---|---|---|---|
| 1,567,931 A | 12/1925 | Epler | |
| 2,852,026 A * | 9/1958 | Erite | A61F 13/53418 604/377 |
| 3,175,558 A * | 3/1965 | Caillonette | A61F 7/03 607/114 |
| 3,809,096 A | 5/1974 | York | |

(Continued)

FOREIGN PATENT DOCUMENTS

| | | |
|---|---|---|
| CA | 2305093 C | 6/2010 |
| CA | 2838148 A1 | 6/2015 |

(Continued)

OTHER PUBLICATIONS

"How to cut a groove or channel on wood" http://theplywood.com/cut-groove-or-channel-without-router (Year: 2018).*

(Continued)

*Primary Examiner* — Ariana Zimbouski
*Assistant Examiner* — Gabriella E Burnette
(74) *Attorney, Agent, or Firm* — Arent Fox, LLP

(57) ABSTRACT

Devices for providing thermal therapy to the perineal and rectal areas of a patient are described. The device is particularly useful for containing gushing lochia flow. Different embodiments of the device can be used to provide either hot or cold therapy to the patient. The inventive thermal pack of the current invention comprises a thermal pouch, pad and a backing layer.

21 Claims, 8 Drawing Sheets

(51) Int. Cl.
  *A61F 7/10* (2006.01)
  *A61F 13/472* (2006.01)
  *A61F 13/513* (2006.01)
  *A61F 13/539* (2006.01)
  *A61F 13/15* (2006.01)
  *A61F 13/51* (2006.01)
  *A61F 13/53* (2006.01)

(52) U.S. Cl.
  CPC ............... *A61F 13/47236* (2013.01); *A61F 13/51305* (2013.01); *A61F 13/539* (2013.01); *A61F 2007/0018* (2013.01); *A61F 2007/0214* (2013.01); *A61F 2007/0226* (2013.01); *A61F 2007/0258* (2013.01); *A61F 2013/1517* (2013.01); *A61F 2013/5103* (2013.01); *A61F 2013/5104* (2013.01); *A61F 2013/51021* (2013.01); *A61F 2013/51045* (2013.01); *A61F 2013/51078* (2013.01); *A61F 2013/530065* (2013.01); *A61F 2013/530481* (2013.01); *A61F 2013/53908* (2013.01)

(58) Field of Classification Search
  CPC ...... A61F 2007/0018; A61F 2007/0214; A61F 2007/0226; A61F 2007/0258; A61F 2013/1517; A61F 2013/51021; A61F 2013/5103; A61F 2013/5104; A61F 2013/51045; A61F 2013/51078; A61F 2013/530065; A61F 2013/530481; A61F 2013/53908; A61F 7/0241; A61F 13/14; A47B 2031/026; A47G 19/027; A61K 9/00; A61K 9/70
  See application file for complete search history.

(56) References Cited

U.S. PATENT DOCUMENTS

| | | | |
|---|---|---|---|
| 3,871,376 A | 3/1975 | Kozak | |
| 4,240,436 A | 12/1980 | Singleton | |
| 4,397,315 A | 8/1983 | Patel | |
| 4,462,224 A | 7/1984 | Dunshee et al. | |
| 4,770,657 A | 9/1988 | Ellis et al. | |
| 4,787,896 A | 11/1988 | Houghton et al. | |
| 4,804,380 A | 2/1989 | Lassen et al. | |
| 4,840,692 A | 6/1989 | Kamstrup-Larsen | |
| 5,167,655 A | 12/1992 | McCoy | |
| 5,178,139 A | 1/1993 | Angelillo et al. | |
| 5,277,180 A | 1/1994 | Angelillo et al. | |
| 5,300,105 A | 4/1994 | Owens | |
| 5,339,541 A | 8/1994 | Owens | |
| 5,357,693 A | 10/1994 | Owens | |
| 5,399,174 A | 3/1995 | Yeo et al. | |
| 5,399,175 A | 3/1995 | Glaug et al. | |
| 5,431,622 A | 7/1995 | Pyrozyk et al. | |
| 5,500,010 A | 3/1996 | Owens | |
| 5,545,198 A | 8/1996 | Owens | |
| 5,575,812 A | 11/1996 | Owens | |
| 5,591,221 A | 1/1997 | Owens | |
| 5,630,959 A | 5/1997 | Owens | |
| 5,643,189 A | 7/1997 | Masini | |
| 5,700,284 A | 12/1997 | Owens | |
| 5,702,375 A | 12/1997 | Angelillo et al. | |
| 5,728,081 A | 3/1998 | Baer et al. | |
| 5,817,149 A | 10/1998 | Owens | |
| 5,817,150 A | 10/1998 | Owens | |
| 5,833,646 A | 11/1998 | Masini | |
| 5,843,067 A | 12/1998 | Trombetta et al. | |
| 5,895,379 A | 4/1999 | Litchholt et al. | |
| 5,935,595 A | 8/1999 | Steen | |
| 5,989,286 A | 11/1999 | Owens | |
| 6,103,139 A | 8/2000 | Kohout | |
| 6,152,952 A | 11/2000 | Owens | |
| 6,225,523 B1 | 5/2001 | Masini | |
| 6,231,555 B1 | 5/2001 | Lynard et al. | |
| 6,233,945 B1 | 5/2001 | Kohout | |
| 6,248,125 B1 | 6/2001 | Helming | |
| 6,251,131 B1 | 6/2001 | Kohout | |
| 6,265,631 B1 | 7/2001 | Angelillo et al. | |
| 6,320,095 B1 | 11/2001 | Wall | |
| 6,393,843 B2 | 5/2002 | Kohout | |
| 6,432,125 B2 | 8/2002 | Kohout | |
| 6,443,936 B1 | 9/2002 | Hamilton et al. | |
| 6,465,712 B1 | 10/2002 | Matthews et al. | |
| 6,479,415 B1 | 11/2002 | Erspamer et al. | |
| 6,524,331 B1 | 2/2003 | Kohout et al. | |
| 6,572,600 B1 | 6/2003 | Roe et al. | |
| 6,599,262 B1 | 7/2003 | Masini | |
| 6,648,909 B2 | 11/2003 | Helming | |
| 6,652,500 B2 | 11/2003 | Daniels et al. | |
| 6,664,435 B2 | 12/2003 | Masini | |
| 6,764,477 B1 | 7/2004 | Chen et al. | |
| 6,770,064 B1 * | 8/2004 | Ruscher | A61F 13/84 604/367 |
| 6,786,880 B2 | 9/2004 | Wall | |
| 6,791,004 B2 | 9/2004 | Sprengard-Eichel et al. | |
| 6,964,803 B2 | 11/2005 | Krautkramer et al. | |
| 6,974,892 B2 | 12/2005 | DeCarvalho et al. | |
| 6,989,471 B2 | 1/2006 | Schmidt et al. | |
| D516,731 S | 3/2006 | Harris | |
| 7,056,311 B2 | 6/2006 | Kinoshita et al. | |
| 7,102,054 B1 | 9/2006 | Cree et al. | |
| 7,626,071 B2 | 12/2009 | Masini et al. | |
| 7,759,540 B2 | 7/2010 | Litvay et al. | |
| 7,795,492 B2 | 9/2010 | Vartiainen | |
| 7,888,547 B2 | 2/2011 | Masini | |
| 7,993,317 B2 | 8/2011 | Hammons et al. | |
| 8,034,991 B2 | 10/2011 | Bruzadin et al. | |
| 8,129,582 B2 | 3/2012 | Jackson et al. | |
| 8,277,432 B2 | 10/2012 | Bergstroem | |
| 8,552,250 B2 | 10/2013 | Robles et al. | |
| 8,569,572 B2 | 10/2013 | Hammons et al. | |
| 8,603,277 B2 | 12/2013 | Paldey et al. | |
| 8,618,351 B2 | 12/2013 | Di et al. | |
| 8,622,982 B2 | 1/2014 | Laugesen et al. | |
| 8,633,347 B2 | 1/2014 | Bianco et al. | |
| 8,636,786 B2 | 1/2014 | Biser | |
| 8,637,728 B2 | 1/2014 | Fingal et al. | |
| 8,669,410 B2 | 3/2014 | Weismantel et al. | |
| 8,729,333 B2 | 5/2014 | Nakatani | |
| 8,766,031 B2 | 7/2014 | Becker et al. | |
| 8,834,441 B2 | 9/2014 | Coates | |
| 8,915,898 B2 | 12/2014 | Dieringer et al. | |
| 8,937,212 B2 * | 1/2015 | Fogg | A61F 13/84 604/378 |
| 8,957,278 B2 | 2/2015 | Kainth et al. | |
| 8,962,911 B2 | 2/2015 | Ehrnsperger et al. | |
| 8,969,651 B2 | 3/2015 | Carlucci et al. | |
| 8,969,652 B2 | 3/2015 | Bewick-Sonntag et al. | |
| D744,661 S | 12/2015 | Rizzi | |
| 9,314,400 B1 | 4/2016 | Dudley | |
| 9,375,346 B1 | 6/2016 | Sundheimer et al. | |
| 9,572,709 B2 | 2/2017 | Fogg et al. | |
| 9,585,794 B2 | 3/2017 | Tsimbler et al. | |
| 2002/0062113 A1 | 5/2002 | Thomas et al. | |
| 2003/0139291 A1 | 7/2003 | Qin | |
| 2004/0243045 A1 | 12/2004 | Masini | |
| 2005/0262871 A1 | 12/2005 | Bailey-Weston | |
| 2006/0287635 A1 | 12/2006 | Angel | |
| 2007/0142807 A1 * | 6/2007 | Lee | A61F 13/84 604/385.01 |
| 2007/0225783 A1 | 9/2007 | Koby et al. | |
| 2008/0039810 A1 | 2/2008 | Lee et al. | |
| 2008/0071336 A1 | 3/2008 | Merriman | |
| 2009/0287282 A1 | 11/2009 | Biser et al. | |
| 2009/0287283 A1 | 11/2009 | Biser et al. | |
| 2010/0217363 A1 | 8/2010 | Whitely et al. | |
| 2010/0298915 A1 | 11/2010 | Whitely et al. | |
| 2011/0319841 A1 | 12/2011 | Romie | |
| 2012/0095424 A1 * | 4/2012 | Komatsu | A61F 13/4756 604/367 |
| 2012/0271267 A1 | 10/2012 | Love et al. | |
| 2013/0267925 A1 | 10/2013 | Aybar et al. | |

(56) References Cited

U.S. PATENT DOCUMENTS

| | | |
|---|---|---|
| 2013/0345657 A1 | 12/2013 | Nelson et al. |
| 2014/0142667 A1 | 5/2014 | Biser et al. |
| 2014/0358108 A1 | 12/2014 | Love et al. |
| 2014/0371828 A1 | 12/2014 | Whitely |
| 2015/0080827 A1 | 3/2015 | Fogg et al. |
| 2015/0150716 A1 | 6/2015 | Whitely |
| 2015/0173942 A1 | 6/2015 | Whitely |
| 2015/0283001 A1* | 10/2015 | Arizti .............. A61F 13/551 206/526 |
| 2015/0297396 A1 | 10/2015 | Whitely |
| 2016/0129626 A1* | 5/2016 | Arora .............. B32B 3/26 264/40.1 |
| 2016/0350828 A1* | 12/2016 | Schmidt .............. A61F 13/84 |
| 2017/0014264 A1 | 1/2017 | Bradley et al. |
| 2017/0079836 A1 | 3/2017 | Mahon |
| 2018/0133071 A1* | 5/2018 | Miao .............. A61F 13/51104 |

FOREIGN PATENT DOCUMENTS

| | | |
|---|---|---|
| EP | 0192687 B1 | 11/1989 |
| EP | 0454912 A1 | 11/1991 |
| EP | 0613357 B1 | 10/1997 |
| EP | 1272228 A1 | 1/2003 |
| KR | 20080039810 A | 5/2008 |
| WO | 9403132 A1 | 2/1994 |
| WO | 9617567 A1 | 6/1996 |
| WO | 9739708 A2 | 10/1997 |
| WO | 9829079 A1 | 7/1998 |
| WO | 0066051 A1 | 11/2000 |
| WO | 0160305 A1 | 8/2001 |
| WO | 0178797 A1 | 10/2001 |
| WO | 03059219 A1 | 7/2003 |
| WO | 2007078328 A2 | 7/2007 |
| WO | 2007148799 A1 | 12/2007 |
| WO | 2009140673 A1 | 11/2009 |
| WO | 2012088310 A1 | 6/2012 |
| WO | 2014151544 A2 | 9/2014 |

OTHER PUBLICATIONS

Neenah Filtration: Meltblown non-wovens. (Year: 2020).*
3M, Material Safety Data Sheet Nexcare™ Instant Cold Packs 2640, 2011, 7 pages.

* cited by examiner

PERINEAL THERMAL PACK WITH IMPROVED LIQUID CONTAINMENT

BACKGROUND

The invention relates generally to thermal therapy devices and relates more specifically to hot and cold pouches and pad combination devices that provide thermal therapy and absorb fluid from the perineal area of a patient.

Various forms of thermal therapy have been used in the past to provide either heating or cooling to specific parts of a patient's body. For example, heat has been used in the past to increase blood flow and speed the healing process to an injured area. Similarly, cooling has been used to prevent and reduce swelling and pain. In the past, hot or cold packs have been used in a variety of applications. One application of particular interest is in providing thermal therapy to postpartum patients in the perineal and rectal areas. This therapy has been provided in a variety of ways.

One recent device includes an elongated pack to provide either heat or cold therapy. The elongated pack also includes a sealed inner space that is enclosed within the outer shell. The sealed space has a first compartment containing a first chemical and a second compartment containing a second chemical. In the preferred embodiment, the first and second compartments are adjacent to one another and are separated by a rupturable wall. When the wall is ruptured, the contents of the two compartments are allowed to mix to create a thermal reaction which produces a temperature in a therapeutic range. In other embodiments, the sealed inner space may be filled with a gel or other material which may be mechanically heated or cooled to a therapeutic temperature range. Although the heating/cooling of this pack may work, absorption of the liquid or blood from the patient is not adequate. Most of the lochia fluid runs off the side of the device and is not absorbed.

Recently, a type of device which has been developed is a combination perineal pad and cold pack in which the cold pack is located on top of the perineal pad. In instances in which the cold pack is fixedly attached to the top of the perineal pad, cooling is readily available, but the cold pack may not be located in the most useful location on the pad. The cold pack film is not appropriate for direct skin contact, and the end seals of the cold pouch are irritating, so there is a nonwoven layer that loosely wraps the cold pouch, or the nonwoven layer loosely wraps the cold pouch and the pad. Also, the pad may not be of the most appropriate size or absorbency for the particular patient's needs.

The combination of a perineal cold pouch and a pad can be used to absorb the lochia fluid flow that occurs following childbirth. After delivery, the patient will undergo a postpartum assessment and fundus examination where the healthcare professional will massage the uterus. This causes gushing flow of lochia to occur. Existing combinations of cold pouch and perineal pad do not effectively contain all of the fluid flow.

It has been found in these previous designs that liquid will flow to the edges of the pad and off the sides without absorbing into the pad core.

A need exists to provide a device which will contain gushing flow of liquid unlike the existing perineal thermal packs.

SUMMARY

Certain aspects of the present disclosure are directed toward a perineal thermal pack with increased fluid containment. The perineal thermal pack can have structural features adapted to provide improved fluid containment, thereby reducing the volume of fluid that is spilled or otherwise not collected into the perineal thermal pack. The improved perineal thermal pack can include modifications such as improved absorbent pad and/or core and thermal pouch attachment, grooves or other similar structures in the pack to aid in liquid collection, attached overwrap at multiple positions on the pad and cold pack, an overwrap that may include slits, additional absorbent material, and backing film edges that fold up. All modifications show significant improvement in liquid containment.

A device is provided for applying thermal therapy to a patient. Specifically, in one embodiment, the thermal therapy is provided to the perineal or rectal area of a patient. The perineal thermal pack contains both a pad that includes an absorbent core and at least a top sheet (and optionally a bottom sheet) and a thermal pouch. The thermal pouch is attached to the pad. The pack includes a backing layer or layers, which preferably comprises a film layer. The pack also comprises optional adhesive means and release tab on the backing film of the absorbent pad. In a preferred embodiment, the thermal therapy is cold therapy.

In one embodiment of the perineal thermal pack, the pad is compressed or thinned where the thermal pouch is attached. There is also an overwrap layer. The overwrap comprises at least one layer, a cover sheet. Additionally, the overwrap can comprise an acquisition distribution layer. The overwrap is attached to the pad beyond the perimeter of the thermal pouch. There are grooves embossed into the overwrap and the pad. The grooves are continuous or discontinuous and can follow the perimeter of the pad.

In another embodiment of the perineal thermal pack, the pad is compressed where the thermal pouch is attached. There is also an overwrap layer. The overwrap comprises at least one layer, a cover sheet. Additionally, the overwrap can comprise an acquisition distribution layer. The overwrap is attached to the pad beyond the perimeter of the thermal pouch, inside the perimeter of the grooves. There are grooves embossed into the pad. The grooves are continuous or discontinuous and follow the perimeter of the pad.

In another embodiment, the perineal thermal pack is comprised of a thermal pouch and a pad, the absorbent material of the pad surrounding the perimeter of the pouch. The absorbent material surrounds the pouch on all four sides. There is also an overwrap layer. The overwrap comprises at least one layer, a cover sheet. Additionally, the overwrap can comprise an acquisition distribution layer. The cover sheet is the top most layer, on the patient facing side.

In another embodiment, the perineal thermal pack is comprised of a thermal pouch with a pad, wherein the backing film of the pack is folded up to act as a guard to contain fluid. The pad is compressed or thinned where the thermal pouch is attached. There is also an overwrap layer. The overwrap comprises at least one layer, a cover sheet. Additionally, the overwrap can comprise an acquisition distribution layer. The cover sheet is the top most layer, on the patient facing side. On the longitudinal edges of the pad, the film edges of the pad are folded up around pad edges and adhered to nonwoven coversheet. The overwrap is attached to the pad beyond the perimeter of the thermal pouch. There are grooves embossed into the overwrap and the pad. The grooves are continuous or discontinuous and follow the perimeter of the pad.

In another embodiment of the perineal thermal pack. The overwrap consists of two layers, an absorbent nonwoven cover sheet and an acquisition distribution layer. The cover sheet is the top most layer, on the patient facing side. The overwrap has at least one slit cut into the overwrap such that fluid can flow from the center of the pack to the edges of the pad. In one embodiment, the slits have a curved shape.

In another embodiment of the perineal thermal pack, a thermal pouch is attached to a pad with a small bubble filled with water attached to the top of the thermal pouch covered by an overwrap that includes a nonwoven cover sheet and an acquisition distribution layer. The small bubble filled with water consists of a perforated or frangible film with water that when activated spreads water over the patient contact area to promote evaporative cooling.

In a preferred embodiment of the perineal thermal pack, a thermal pouch is embedded in the pad. The pad comprises an absorbent core and a surrounding sheet comprised of a top and bottom sheet. In one embodiment, at least one sheet is a nonwoven. The core has a void center portion and the top and bottom sheet are attached together at the void. The opening is substantially similar in dimensions to the size of the pouch. In one embodiment, the dimensions of the void is the same size or smaller than the size of the thermal pouch. The cold pouch is inserted underneath the top and bottom sheets. The top and bottom sheets are fully secured to the core with adhesive, except where the cold pouch is present. The top and bottom sheets are secured to the cold pouch. The device also has a backing layer. The backing layer can comprise multiple layers and at least comprises a film layer. The backing layer is below the cold pouch and pad.

This invention also includes a process for manufacturing the perineal cold pack. In a preferred embodiment, an absorbent core is made on an airlaid machine. The resulting rolls of core are cut to the size and shape of the current invention. First, an outer rectangle is cut, and then an inner rectangular window is removed from the center of the rectangle. The windowed cores are then wrapped in a nonwoven sheet. The sheet is secured to the fluff pulp on both sides with adhesive. The two layers of nonwoven core wrap are then adhered to each other in the window area where there is no core. The top of a thermal cold pouch is then glued to the back of the top and bottom sheet wrapped core in the window lacking absorbent core, such that the end seals of the thermal pouch are covered by the core when the product is viewed from the top. The pouch was secured throughout the top/side areas so that fluid containment areas form around the perimeter of the core void area. A backing layer is adhered to the bottom of the cold pouch and the bottom of the wrapped core using an adhesive.

In another embodiment, an absorbent core is made with a core forming machine and includes a window. The windowed cores are then wrapped in a sheet. The sheet is secured to the fluff pulp on both sides with adhesive. The two layers of nonwoven core wrap are then glued to each other in the window area where there was no core. The top of a thermal cold pouch is then glued to the back of the top and bottom sheet wrapped core in the window lacking absorbent core, such that the end seals of the thermal pouch are covered by core when the product is viewed from the top. The pouch was secured throughout the top/side areas so that fluid containment areas form around the perimeter of the core void area. A backing layer is adhered to the bottom of the cold pouch and the bottom of the wrapped core using an adhesive.

Any feature, structure, or step disclosed herein can be replaced with or combined with any other feature, structure, or step disclosed herein, or omitted. Furthermore, for purposes of summarizing the disclosure, certain aspects, advantages, and features of the devices have been described herein. It is to be understood that not necessarily any or all such advantages are achieved in accordance with any particular embodiments disclosed herein. No individual aspects of this disclosure are essential or indispensable.

BRIEF DESCRIPTION OF THE FIGURES

Embodiments of the present disclosure are described by way of following drawings pointing out the various details of the device and method of the present disclosure. The main features and advantages of the present disclosure will be better understood with the following descriptions, claims, and drawings, where:

DETAILED DESCRIPTION

Figure 1:
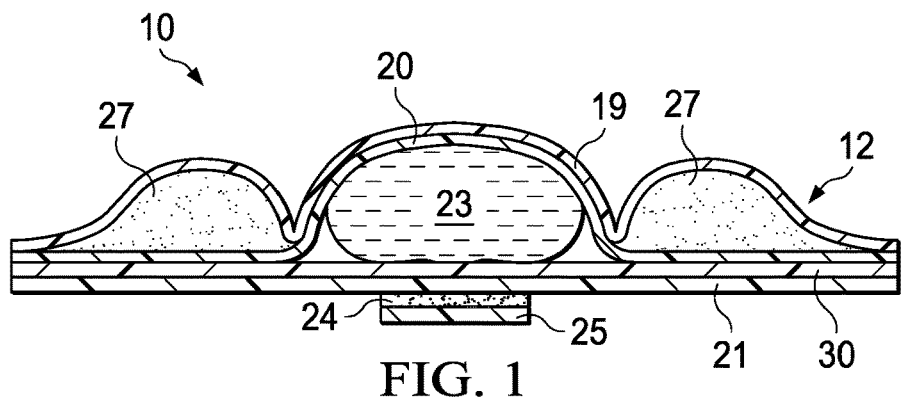
FIG. 1 is a cross section view of an exemplary embodiment of the current application.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

Various aspects of a perineal thermal pack may be illustrated by describing components that are connected, coupled, attached, bonded and/or joined together. As used herein, the terms "connected", "coupled", "attached", "bonded" and/or "joined" are used interchangeably to indicate either a direct connection between two components or, where appropriate, an indirect connection to one another through intervening or intermediate components.

Relative terms such as "lower" or "bottom", "upper" or "top", and "vertical" or "horizontal" may be used herein to describe one element's relationship to another element illustrated in the drawings. It will be understood that relative terms are intended to encompass different orientations of the perineal thermal pack in addition to the orientation depicted in the drawings.

Reference will be made to figures wherein like structures are provided with like reference designations. It should be understood that the figures are diagrammatic and schematic representations of exemplary embodiments of perineal thermal pack of the present disclosure, and are neither limiting nor necessarily drawn to scale.

A device is provided for applying thermal therapy to a patient. In a preferred embodiment, the thermal therapy is applied to the perineal or rectal area of a patient. The perineal thermal pack contains both a pad and a thermal pouch. The pad includes an absorbent core and a surrounding sheet that comprises a top and a bottom sheet. The thermal pouch is attached to the pad. The pack also can include an overwrap, which comprises at least one layer. The pack includes a backing layer. The pack also comprises optional adhesive means and release tab on the backing layer.

Thermal Pouch

Any thermal insert can be utilized in the described invention. In a preferred embodiment, the insert is a thermal pouch.

Any thermal pouch known in the art can be utilized in the current invention.

In the preferred embodiment, a sealed inner space is provided, referred to as the thermal pocket. The sealed inner space can be a polyolefin or combination of multiple polyolefins. The sealed inner space can be formed of a pouch made of a laminated roll stock, polyester/low-density polyethylene (LDPE). Other materials which may be used to form the pocket include biaxially oriented nylon laminated, linear low density polyethylene (LLDPE), polyethylene, polypropylene, and co-polymers of polyolefins. The thermal pouch can be an embossed or thermoformed film. Any material known in the art can be used for the thermal pouch.

The inner space includes a first compartment which contains a first chemical. The inner space also includes a second compartment containing a second chemical. A rupturable wall is also provided between the first and second compartments. When the rupturable wall is ruptured, the first and second chemicals are allowed to mix to cause either an endothermic or exothermic reaction to occur. When heat therapy is desired, the first chemical may be taken from the group consisting of sodium acetate and sodium thiosulfate, and the second chemical may be taken from the group consisting of borax and aluminum oxide so that when the first and second chemicals are exposed, an exothermic crystallization of a supersaturated solution occurs.

Similarly, when cold therapy is desired, the first chemical may be taken from the group consisting of calcium ammonium nitrate, ammonium nitrate, aluminum chloride, and urea, and the second chemical may be taken from the group consisting of water and additives so that when the first and second chemicals are mixed, an endothermic dissolution reaction occurs.

In one embodiment, the first compartment is formed of a rupturable sealed bubble. The bubble is located entirely within the sealed pouch. The second compartment is formed from an area remaining between the sealed bubble and the inner wall of the pouch. Accordingly, the bubble contains the first chemical, and area contains the second chemical. For example, bubble may contain water, and area may contain ammonium nitrate. In another embodiment the bubble may contain ammonium nitrate and the area may contain water. When the bubble is ruptured, the ammonium nitrate and water mix to produce an endothermic dissolution reaction, resulting in cooling. In another embodiment of the invention, the outer shell of the device is formed from first and second sheets of a fluid impervious material. The first and second sheets are sealed to one another around the edges to form a sealed inner space. A third rupturable sheet is located between the first and second sheets. The third sheet is sealed to at least one of the first and second sheets around the edges of the third sheet so that a first compartment is formed by an area between the first and third sheets and a second compartment is formed in the area between the second and third sheets.

Another embodiment of the thermal pouch is a device formed from two sheets of material. A first sheet is used to form an outer shell. A second sheet of material is a rupturable material. The second sheet is sealed about its edges to the first sheet to form a first compartment. The first sheet is then folded over the second sheet and sealed about its edges to form a second compartment. First and second chemicals are inserted in the first and second compartments respectively.

In a particularly preferred embodiment, the first compartment is formed from a bubble made of laminated film made of polyester/LDPE and is filled with water. The second compartment is formed from a second single sheet of mLLDPE (linear low density polyethylene) polymer. The second sheet is folded to surround and encase the bubble. The second sheet is sealed along its opposite folded edges to form an envelope type pouch which forms the second compartment. The second compartment is then filled with ammonium nitrate. The remaining edges between the opposite folded edges are then sealed to seal the second compartment. In the preferred embodiment, the bubble has a perforated area which weakens the bubble and allows it to rupture prior to any rupturing of the second sheet. Thus, when pressure is applied to the device, the perforated area will rupture first to allow the water and ammonium nitrate to mix, thereby producing the desired endothermic reaction. In other similar embodiments, other chemicals may be used as described above to produce an exothermic reaction. The amount of air present in both compartments is minimized.

The thermal pouch may be removable or permanent. In a preferred embodiment, the thermal pouch is not removable and, therefore, permanent.

The thermal pouch for the described invention can include any of the preferred embodiments described above or any of those known in the art. In a preferred embodiment, the thermal pouch is a cold therapy pouch.

Absorbent Pad

In certain embodiments, a pad can be utilized. The pad is comprised of an absorbent core and a surrounding sheet. The sheet can be comprised of a top sheet and a bottom sheet. There can also be only a top sheet or bottom sheet.

The absorbent core will normally have one or more layers of absorbent material which may be contained within a wrapper. Examples of suitable unmodified/modified naturally occurring fibers that can be used in the absorbent core include cotton, Esparto grass, bagasse, kemp, flax, silk, wool, wood pulp, chemically modified wood pulp, jute, rayon, ethyl cellulose, and cellulose acetate. Gauze, tissue or synthetic polymer foam may also be used. Cellulosic fibers, in particular wood pulp fibers, are a preferred element for use in the present invention. Optionally the core may contain superabsorbent polymer (SAP) mixed in with the cellulosic fibers.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemomechanical, and chemothermomechanical pulp processes. Recycled or secondary wood pulp fibers, as well as bleached and unbleached wood pulp fibers, can be used.

The absorbent core can be formed in a variety of different ways. For example, the core can be formed using a hammer mill and a core forming drum, or the core can be formed using an airlaid machine.

Airlaid cores are generally preferred, especially for the embossed design. The airlaid cores are made with mixtures of absorbent (typically cellulosic) natural fibers and thermoplastic bonding fibers, or other core binders that make the core grooves and recessed area where the thermal pack is placed easier to form and hold in place thru the application of heat and/or pressure, activating the binder during the embossing. An airlaid core with bonding fibers or binders is a good method for making the core because the thermal pouch overwrap layer(s) can pull up in the z direction where they are bonded to the absorbent core. With a drum formed fluff pulp core this z directional pulling can pull up on the absorbent pad top sheet, and even pull apart the unbonded fluff pulp, greatly reducing or eliminating the liquid containment grooves, and reducing the core liquid absorption rate in the areas where the thermal pouch overwraps pull up on the core. Airlaid cores have a thermoplastic binder or bonding fibers, and this helps to better set the embossed grooves, and the core is able to better resist this overwrap z directional pulling force.

The liquid pervious sheet over the absorbent-core is normally a soft fabric. A suitable sheet or sheets may be manufactured from a wide range of materials, such as porous foams, reticulated foams, apertured plastic films; or woven or nonwoven webs of natural fibers, synthetic fibers, or a combination of natural and synthetic fibers.

Generally, the top and/or bottom sheets are compliant, soft feeling, and non-irritating to the wearer's skin. Further, the sheet(s) are liquid pervious permitting liquids to readily penetrate through their thickness. Provided it will satisfy the requirements as laid out later, a suitable sheet(s) may be manufactured from a wide range of materials, such as porous foams, reticulated foams, apertured plastic films; or woven or nonwoven webs of natural fibers, synthetic fibers, or a combination of natural and synthetic fibers.

In a preferred embodiment, the top and bottom sheets are nonwoven. The nonwoven top and bottom sheets can be pliant, nonwoven, and fluid and liquid pervious.

The nonwoven webs may be wet laid, dry laid, spunlaced, adhesive bonded, thermal bonded or spunmelt nonwoven including spunbond or spunbonded-melt blown-spunbonded (SMS) web types. The webs may be made of thermoplastic fibers, regenerated fibers, natural fibers, and so-called bicomponent or sheath-core fibers, and may comprise mixtures of any two or more of the foregoing fiber types. Common synthetic fibers are polypropylene, polyethylene, polyesters, nylons, and the most common natural fibers are composed of cellulose. Other materials include carded nonwovens, carded cellulose+synthetic fiber nonwovens that are bonded in a variety of different ways. One specific example is 50 gsm Suominen thermally bonded 20% viscose, 80% polypropylene carded nonwoven. Top sheet nonwovens can also be perforated to help enable liquid to pass thru the nonwoven. Embossed nonwovens can also be used as a top or bottom sheet.

Preferably the top and/or bottom sheets according to the current invention comprises a means to adjust hydrophilicity of the material.

In case of nonwoven sheets, this can be done by adjusting the surface energy of the fibers before the nonwoven is formed, or by adjusting the surface energy of the nonwoven after it is formed. The hydrophilicity adjustments can be made such that they do not wash away easily upon wetting such as with urine, or, which is more preferred, such that they remain effective even at repeated wettings, though may be at a reduced level. In a preferred embodiment, this is done by applying surfactant to the nonwoven top sheet. The surfactant can be applied continually or non-continually in any type of pattern or zone. The surfactant can be applied in zones across web where absorbency is required.

The nonwoven material top and/or bottom sheets can be formed from surfactant-treated spunbond polyolefin. In a preferred embodiment, the nonwoven top layer is formed from surfactant-treated spunbond polypropylene.

The top sheet and bottom sheet can also be comprised of a film. The film can be fluid and liquid impervious.

There are various arrangements for the pad and thermal pouch in the current pack. The pad and pouch can be attached to one another by any means. In one embodiment, the pad and the pouch are joined by adhesive. In one embodiment, the pad is compressed where the thermal pouch is attached. In another embodiment, the backing layer on the pad can be folded up and attached to the overwrap. In another embodiment, part or all of the absorbent core can be removed from the location where the thermal pouch is to be attached. The thermal pouch can then be inserted in this area. In a particular embodiment, the portion of the pad removed can be the fluff pulp material. In another embodiment, the absorbent core can be formed so that less or no absorbent material is located where the thermal pouch is attached, creating a recessed area.

The pad can be any size or shape. In a preferred embodiment, the pad is larger in length and width than the pouch. The pouch can also be any size or shape. In some embodiments, the pad and pouch are rectangular in shape. In other embodiments, the pouch and pad have an hourglass or contoured shape. In another embodiment, the pouch is rectangular and the pad has an hourglass or contoured shape.

In the embodiments where a portion of the absorbent core of the pad is removed, the pouch may be at least as large as the void (removed portion). In some embodiments the pouch is larger than the void.

Backing Layer

The backing layer of the current invention comprises at least one layer. In one embodiment the backing layer comprises two layers.

The backing layer preferably comprises a film layer. The film layer is normally a thin flexible plastic film. Polymer films which may be used herein include olefinic polymers and copolymers, polyester polymers and copolymers and polyamide polymers and copolymers. Olefinic polymers and copolymers may include polyethylenes; polypropylene; ethylene-propylene copolymers; copolymers of ethylene with other ethylenically unsaturated monomers such as vinyl halides, vinyl acetate, vinylidene halides, vinyl alcohol, styrene, (meth)acrylic acid, esters of (meth)acrylic acid and acrylonitrile; and rubbery copolymers such as ethylene-propylene rubber (EPR), ethylene propylene diene rubber (EPDM), styrene-acrylonitrile rubber (SAR), styrene-butadiene rubber (SBR), and acrylonitrile-butadiene elastomeric copolymers (BAN). The films may be cast films, extruded films or blown films. Vapor deposited or metallized polymer or metal films may also be used as the film layer. In one embodiment of the current invention, the film layer is pliant and fluid impervious. In a preferred embodiment of the current invention, the film layer is polypropylene.

The backing layer may further comprise a nonwoven sheet layer. The nonwoven sheet layer can be pliant.

The nonwoven webs may be wet laid, dry laid, spunlaced, adhesive bonded, thermal bonded or spunmelt nonwoven including spunbond or spunbonded-melt blown-spunbonded (SMS) web types. The webs may be made of thermoplastic fibers, regenerated fibers, natural fibers, and so-called bicomponent or sheath-core fibers, and may comprise mixtures of any two or more of the foregoing fiber types. Common synthetic fibers are polypropylene, polyethylene, polyesters, nylons, and the most common natural fibers are composed of cellulose. Other materials include carded nonwovens, carded cellulose and synthetic fiber nonwovens that are bonded in a variety of different ways. One specific example is 50 gsm Suominen thermally bonded 20% viscose, 80% polypropylene carded nonwoven.

The film layer of the backing layer can be joined to the pad. The film layer of the backing layer can also be joined to the absorbent core. The backing layer can also be joined to the cover sheet. Any suitable attachment means can be used for joining the backing layer to the pad, the absorbent core, the cover sheet or all. The pad can also be attached to the cover sheet and the backing layer or both. Any suitable attachment means can be used for joining the pad to the coversheet or the backing layer or both.

Additional Absorbent Material

Additional absorbent material can be added on top of the pad, surrounding the thermal pouch. The absorbent material can be any known absorbent material. In one embodiment, the absorbent material can be multiple layers of absorbent material. In another embodiment, the absorbent material can be rolled up absorbent material. In a preferred embodiment, the absorbent material is a hydrophilic nonwoven. In a further embodiment, the absorbent material can be foam material.

The absorbent material can be on any side of the thermal pouch. In one embodiment, the absorbent material is on the two longitudinal sides of the pouch. In another embodiment, the absorbent material is on all four sides of the pouch.

The additional absorbent material can be at any level in comparison to the thermal pouch. In a preferred embodiment, the absorbent material is at the same height level as the activated thermal pouch. In another preferred embodiment, the absorbent material is at a height higher than the activated thermal pouch.

Overwrap

In some embodiments, an overwrap is above the pad and thermal pouch, facing the patient. In other embodiments, an overwrap is surrounding the pad and thermal pouch.

The overwrap comprises at least one layer. In one embodiment, the overwrap comprises at least two layers.

The overwrap can include a cover sheet. The overwrap can also include an acquisition distribution layer. In an embodiment, the cover sheet is above the acquisition distribution layer, facing the patient.

Overwrap layer(s) can be joined to the pad and backing layer with an adhesive. Overwrap layer(s) are attached the pad at multiple points, including right outside the perimeter of the cold pouch. The overwrap can also be fully attached to the pad in all areas but that of the cold pouch.

Cover Sheet

The cover sheet can be the top layer, facing the patient. The cover sheet can be absorbent material.

Generally, the cover sheet is compliant, soft feeling, and non-irritating to the wearer's skin. Further, the cover sheet is liquid pervious permitting liquids to readily penetrate through its thickness. Provided it will satisfy the requirements as laid out later, a suitable cover sheet may be manufactured from a wide range of materials, such as porous foams, reticulated foams, apertured plastic films; or woven or nonwoven webs of natural fibers, synthetic fibers, or a combination of natural and synthetic fibers.

In a preferred embodiment, the cover sheet is a nonwoven. The nonwoven cover sheet can be pliant and fluid pervious.

The nonwoven webs may be wet laid, dry laid, spunlaced, adhesive bonded, thermal bonded or spunmelt nonwoven including spunbond or spunbonded-melt blown-spunbonded (SMS) web types. The webs may be made of thermoplastic fibers, regenerated fibers, natural fibers, and so-called bicomponent or sheath-core fibers, and may comprise mixtures of any two or more of the foregoing fiber types. Common synthetic fibers are polypropylene, polyethylene, polyesters, nylons, and the most common natural fibers are composed of cellulose. Other materials include carded nonwovens, carded cellulose and synthetic fiber nonwovens that are bonded in a variety of different ways. One specific example is 50 gsm Suominen thermally bonded 20% viscose, 80% polypropylene carded nonwoven. Cover sheet nonwovens can also be perforated to help enable liquid to pass thru the nonwoven. Embossed nonwovens can also be used as a cover sheet.

Preferably the cover sheet according to the current invention comprises a means to adjust hydrophilicity of the material.

In case of nonwoven cover sheets, this can be done by adjusting the surface energy of the fibers before the nonwoven is formed, or by adjusting the surface energy of the nonwoven after it is formed. The hydrophilicity adjustments can be made such that they do not wash away easily upon wetting such as with urine, or, which is more preferred, such that they remain effective even at repeated wettings, though may be at a reduced level. In a preferred embodiment, this is done by applying surfactant to the nonwoven cover sheet. The surfactant can be applied continually or non-continually in any type of pattern or zone. The surfactant can be applied in zones across web where absorbency is required.

The nonwoven material cover sheet can be formed from surfactant-treated spunbond polyolefin. In a preferred embodiment, the nonwoven cover sheet is formed from surfactant-treated spunbond polypropylene.

Acquistion Distribution Layer

The overwrap may also comprise an acquisition distribution layer. Materials which may be used to form the acquisition distribution layer are tissue, apertured film, perforated nonwoven, or carded or wet laid cellulose and synthetic fiber nonwovens. The nonwoven webs may be wet laid, dry laid, spunlaced, adhesive bonded, thermal bonded or spunmelt nonwoven including spunbond or spunbonded-melt blown-spunbonded (SMS) web types. The webs may be made of thermoplastic fibers, regenerated fibers, natural fibers, and so-called bicomponent or sheath-core fibers, and may comprise mixtures of any two or more of the foregoing fiber types.

In one embodiment, the acquisition distribution layer can be pliant and fluid pervious.

In a preferred embodiment, the acquisition distribution layer is formed from thermally bonded cellulose and polypropylene (Suominen thermal bond grade BE149909). In another embodiment, the acquisition distribution layer can be formed from spunbond polypropylene.

The nonwoven top cover sheet and the acquisition distribution layer can be applied to the pad/pouch separately or as a single overwrap adhered thermally or with adhesive. In a preferred embodiment, the nonwoven top cover sheet and the acquisition distribution layer are adhered together as a single overwrap.

The overwrap layer or layers can include slits in any pattern or shape. The slits can be such that fluid can from the center of the perineal thermal pack to the pad edges. In one preferred embodiment, the slits have a curved shape.

Adhesive Layers

One of more adhesive layers can be utilized in the embodiments of the current invention.

The adhesive layers can be the same adhesive, or different.

The adhesive layer used in any embodiment can be any of those known in the art.

The adhesives used in any of the embodiments can also comprise thermoplastic adhesives, thermosetting adhesives and/or crosslinked adhesives. Illustrative thermoplastic adhesives include olefinic polymer and copolymer adhesives, such as ethylene vinyl acetate, styrene, maleic anhydride modified polyethylene or polypropylene; polyamide adhesives, polyester and polyurethane adhesives. Illustrative thermosetting adhesives may include (meth)acrylic adhesives or styrene adhesives. Other adhesives conventionally employed in the field of nonwovens may also be used.

Thermoplastic hot melt adhesives are generally preferred. The hot melt adhesives may comprise ethylene vinyl acetate, styrene, polyolefins, modified polyolefins, polyamides and/or polyesters. Any suitable adhesive may be used, especially those known in the art for hygiene product manufacturing.

The adhesive can also be a pressure sensitive adhesive. A pressure sensitive adhesive can be any suitable adhesive including pressure-sensitive adhesives (PSAs) and heat activated adhesives. Useful PSAs include rubber based adhesives, acrylic adhesives, vinyl ether adhesives, silicone adhesives, and mixtures of two or more thereof.

In a preferred embodiment, one adhesive is a petroleum-based adhesive.

The packs of the current invention can include an adhesive layer on the bottom layer of the back layer and optional release liner.

Grooves or Channels

The assembled thermal pack can include grooves, channels, embossed pattern, embossment, depression or the like in the area between the outermost edge of the pad and the thermal pouch. In one embodiment, the assembled thermal pack has grooves. The grooves can be embossed into the pad and overwrap or just into the pad. Preferably, the grooves are embossed into the pad and overwrap. The thermal pack overwrap layers are bonded together and then pushed into the embossed grooves and adhered in the groove using some sort of bonding method: a hot melt glue or tape, pressure, thermal bonding, ultrasonic bonding or a combination of these. In another embodiment, the groove is cut into the pad core and extends completely through the thickness of the pad. The grooves can be continuous or discontinuous. In a preferred embodiment, the grooves are continuous. The grooves can also be formed in any shape or pattern. In a preferred embodiment, the grooves are in the shape of the perimeter of the pad. The groove cross-section can be any shaped including 'V' or 'U' shaped. In a preferred embodiment, the groove cross-section is 'U' shaped. The depth of the groove can extend 25% or more into the thickness of the pad. In a preferred embodiment, the depth of the groove extends 50% or more into the thickness of the pad.

It is preferred that in the current invention the device is arranged such that there are not any loose portions of the overwrap or top or bottom sheets that would create a tent-like or unattached sheet. This improves the flow of the liquid in to the absorbent core of the pad through capillary action.

In one embodiment of the perineal thermal pack, a thermal pouch is attached to a pad with a small bubble filled with water attached to the top of the thermal pouch covered by one or more absorbent nonwoven layers. The small bubble filled with water consists of a perforated or frangible film with water that when activated spreads water over the patient contact area to promote evaporative cooling. In another embodiment the small bubble can be attached to the inside off the dustcover outerwrap. It can also contain a therapeutic agent to help aide comfort and healing.

In a preferred embodiment, an absorbent core is made on an airlaid machine. The core can be Georgia Pacific series 4881 fluff pulp. The resulting rolls of core were cut to the size and shape of the current invention using a die press machine and die cutter. First, an outer rectangle is cut, and then an inner rectangular window is removed from the center of the rectangle. Cores can range from 0.41 to 0.79 inches in thickness, and 611 to 1125 gsm in basis weight. The windowed cores are then wrapped in a sheet. The sheet is secured to the fluff pulp on both sides with adhesive. In a preferred embodiment this is applied using a spiral spray hot melt glue gun. The two layers of nonwoven core wrap are then glued to each other in the window area where there was no core.

The top of a thermal cold pouch is then glued to the back of the top sheet wrapped core in the window lacking absorbent core, such that the end seals of the thermal pouch are covered by core when the product is viewed from the top. An adhesive is applied to glue the wrapped pad nonwoven to the thermal pouch. The pouch was secured throughout the top/side areas so that fluid containment areas form around the perimeter of the core void area. A backing film layer is glued to the bottom of the cold pouch and the bottom of the wrapped core using an adhesive, preferably a hot melt. The fluid containment areas along the length of the cold pouch can optionally be enhanced by heat sealing the nonwoven in the window area adjacent to the long edges of the cold pouch to the backing film, forming deeper fluid containment channels. This heat sealing can be done electronically.

In another preferred embodiment, an absorbent core is made on an airlaid machine. The core can be Georgia Pacific series 4881 fluff pulp. The resulting rolls of core are cut to the size and shape of the current invention using a die press machine and die cutter. The core is formed as a window. Cores can range from 0.41 to 0.79 inches in thickness, and 611 to 1125 gsm in basis weight. The windowed cores are then wrapped in a sheet. The sheet is secured to the fluff pulp on both sides with adhesive. In a preferred embodiment this is applied using a spiral spray hot melt glue gun. The two layers of nonwoven core wrap are then glued to each other in the window area where there was no core.

The top of a thermal cold pouch is then glued to the back of the top sheet wrapped core in the window lacking absorbent core, such that the end seals of the thermal pouch are covered by core when the product is viewed from the top. An adhesive is applied to glue the wrapped pad nonwoven to the thermal pouch. The pouch was secured throughout the top/side areas so that low fluid containment areas form around the perimeter of the core void area. A backing film layer is glued to the bottom of the cold pouch and the bottom of the wrapped core using an adhesive, preferably a hot melt.

Fluid Containment Testing

A test method was developed to evaluate gushing flow fluid containment by using a separatory funnel filled with 50 mL of synthetic blood. The synthetic blood mimics the fluid properties and coloring of actual blood, and is purchased from Johnson, Moen, & Co. Inc. The sample cold pouches were activated by folding them in halt inward toward the pouch until the water bubble broke. The product was shaken to mix the water with the ammonium nitrate (AN). The activated perineal thermal pouch was laid flat on a pre-weighed underpad and the stem of the separatory funnel was placed over the center of the product, with a vertical distance of 5 to 10 mm between the bottom of the stem and the top of the product. Fluid was introduced by fully opening the stopcock. The flow rate was approximately 10 mls/second. The amount of blood that leaked off the pad was evaluated by re-weighing the underpad. The commercially available products contained very little blood, most of it flowed right off the pad during testing. Most embodiments of the current invention tested in this way contained all of the blood within the pad. All embodiments contained greater than 70% of the blood in the pad. Preferred embodiments contained at least 90% of the blood in the pad. All embodiments did not have any fluid present on the bottom outward facing side of the product.

Prototype Construction

Window Frame Design

Absorbent fluff pulp cores of varying densities and thicknesses were made on an airlaid machine. The fluff pulp was Georgia Pacific series 4881 fluff pulp. The resulting rolls of fluff pulp were cut to the size and shape of the current invention using a die press machine and die cutter. First, a rectangle of 12 by 4.5" was cut, and then an inner rectangular window of 8.5 by 2.5" was removed from the center of the rectangle. Cores ranged from 0.41 to 0.79 inches in thickness, and 611 to 1125 gsm in basis weight. The samples were wrapped in 12 gsm durable surfactant treated spunbond polypropylene (SBPP) nonwoven (top and bottom nonwoven sheets), which was secured to the fluff pulp on both sides with a hygiene construction grade adhesive (Henkel TECHNOMELT DM 898B) applied using a spiral spray hot melt glue gun. The two layers of nonwoven sheets were glued to each other in the window area where there was no fluff pulp.

Thermal pouches were fabricated from 3.5 mil monolayer white mLLDPE non-treated film. The film was formed into a 9.5 by 2.75" pouch using a heat sealer, and one end was left open. 57 grams ammonium nitrate (AN) and a water bubble were added to the thermal pouch before sealing it closed on the heat sealer. The water bubble was formed using PPS perforated film consisting of 48 ga polyester, 6.0 ga saran, and 2.0 mil LDPE. When bent, the perforated film breaks, releasing the water to mix with the AN, which causes a decrease in temperature. The film was formed into a [8 by 1.625"] bubble using a heat sealer. 85 grams of water was sealed into each bubble with minimal air. After the AN and water bubble were added to the thermal pouches, the pouches were sealed closed with minimal air inside using the heat sealer.

The top of a thermal cold pouch was glued to the back of the spunbond-wrapped fluff pulp core in the window lacking fluff pulp, such that the end seals of the thermal pouch were covered by the fluff pulp core when the product is viewed from the top. A spiral spray construction grade hot melt was applied to glue the wrapped pad nonwoven to the thermal pouch. The pouch was secured throughout the top/side areas so that fluid containment areas form around the perimeter of the fluff void area. A bilaminate back sheet was fabricated by gluing a sheet of 25 gsm untreated hydrophobic spunbond polypropylene nonwoven to a sheet of 12 gsm polypropylene (PP) film. The bilaminate film side was glued to the bottom of the cold pouch, which was the side of the pouch with the longitudinal fin seal, and the bottom of the wrapped core using a spray gun and construction grade hot melt, helping to secure the thermal pouch to the fluff pulp core.

Embossed Channel/Groove Design

Absorbent fluff pulp cores of varying densities and thicknesses were made on an airlaid machine. The resulting rolls of fluff pulp were cut to a 12 by 4.5 inch rectangular shape using a die press machine. The rectangular fluff pulp cores were wrapped in 12 gsm durable surfactant treated SBPP nonwoven, which was secured to the fluff pulp on both sides with hygiene construction grade adhesive applied using a spiral spray hot melt glue gun. Enough hot melt was sprayed on the top of the core fluff pulp so that the top sheet would stay attached to the fluff pulp when channels were embossed into the core. The bottom of the cold pouch was glued to the top nonwoven layer of the pad. A 17 gsm durable surfactant SBPP cover sheet nonwoven was placed over the pouch and glued to the pad top sheet everywhere except for the top of the pouch. A deep channel was embossed around the perimeter of the cold pouch using a hydraulic press and a stainless steel u-channel. The u-channel embossing fixture edges were laser cut to make them flat. The width of the edge used for embossing was 0.1875 inches wide. The u-channel was placed over the coversheet and pouch and deep channels were embossed around the perimeter of the pouch by pressing the u-channel into the pad using 4100 psi for 30 seconds using a hydraulic press. The embossing fixture width was 3 inches, and it was centered over the middle of the pad. Placing the channels approximately ¾ of an inch from the edge of the core on the sides of the pad. End channels were also embossed ¾ of an inch in from the end of the core. A 12 gsm PP hygiene film back sheet was glued to the back side of the pad using the spray gun and construction hot melt.

Airlaid Core Sample Design

Sample A1:

A 7×13 inch sample of the same airlaid core used in sample A3 (below) was slit down the center 9.5 inches of the core. Two 3.0 inch wide cuts were made perpendicular on end of the 9.5 inch long center slit, the center slit bisecting the 3 inch cross slits. The slits look like the capital letter I. The airlaid core was folded back on itself in the 9.5 in long slit area and this folded over portion hot melted to itself to form double thickness that was 1 inch wide on each side down the length of the 9.5 inches. This resulted in a void area (window) for the cold pack insertion that was 2.50 inches wide by 9.50 inches in length. The total pad core dimension was 7.5×13 inches. The core window was placed over the cold pouch. A 17 gsm SBPP cover sheet was glued to the top of the pouch and the entire top surface of the airlaid core. Hot melt was applied to the cold pouch so that the cover sheet followed the curvature of the cold pouch, creating fluid collection areas at the edges where the cold pouch was contacting the inside perimeter of the core void. The film side of 12 gsm PP hygiene film plus 25 gsm untreated SBPP bilaminate back sheet was glued the back of the airlaid core and the bottom of the cold pouch.

Sample A2:

This sample was prepared similar to sample A1 with following exceptions. The airlaid core was a 7⅞ths×11⅞ inch piece of Glatfelter MH300.100 hybrid bonded airlaid with SAP. The airlaid basis weight was 300 g/m2 and the thickness was 3.2 mm (0.125 inches), with 17 g/g absorbency. The core was slit and folded back onto itself as in sample A1, and then 1.25 inches from each outward edge were folded inward from the edge along the entire length of the pad and glued to itself and glued to the folded outward flap from the center hole. This resulted in a 9.5 inch area that was three layers of airlaid running along the length of the opening for the cold pouch, with two layers of thickness beyond the 9.5 inch length to the end of the pad core.

Sample A3:

Thermally bonded airlaid core was made with 10% hydrophilic treated Trivera bicomponent PE/PET bonding fibers and 90% fluff pulp. The airlaid core was 210 gsm and 0.25 inches thick. An 8.5×12 inch piece of airlaid core was rolled inward at the outside edges and heat sealed together on a ¼ inch wide bar sealer forming channels the entire length of the core. The folded overlapped width was 1.25 inches including the heat seal. The resulting pad core measured 5.5 inches wide by 12 inches long, with 2 thickness of airlaid core 1.25 inches wide along both edges of the pad, and a single thickness of airlaid core in the middle of the pad. The width between the inside edges of the heat sealed channels was 3 inches apart. A cold pouch was centered between the channels and glued to the airlaid core. A 17 gsm hydrophilic surfactant treated SBPP cover sheet was glued to the top of the cold pouch, and to the pad core. A 12 gsm PP hygiene film was glued to the back of the pad.

Sample A4:

The core was constructed using Glatfelter airlaid grade MH300.108 a 300 gsm 3.20 mm thick hybrid bonded airlaid with SAP, and 17 g/g absorbent capacity. A 7⅞th×11⅞ inch sheet of airlaid was used to construct the core. The construction was similar to similar to sample A3, except that the total width of the pad core was 5 inches and the folded in overlap was 1⅜ths inches on each side including the ¼ inch width of the thermal seal which ran the entire length of the core.

TABLE 1

Prior Art Examples

| Prior Art Product | Catalog Number | % Fluid Contained | Fluid present on bottom outward facing side of product? |
|---|---|---|---|
| Cardinal Basic | 115500-010 | 79 | Yes |
| | | 73 | Yes |
| | | 93.2 | Yes |
| Cardinal Premium | 11447-010 | 22.8 | Yes |
| | | 12 | Yes |
| | | 54 | Yes |
| Centurion | CN14230 | 73 | Yes |
| | | 47.6 | Yes |
| | | 55 | Yes |
| Medi-Choice | 69902 | 71.2 | Yes |
| | | 73.4 | Yes |
| | | 72.8 | Yes |
| Medline Green | MDS 138055 | 78.8 | Yes |
| | | 42.4 | Yes |
| | | 50.2 | Yes |
| Medline Premium | MDS 158055 | 61.6 | Yes |
| | | 36.2 | Yes |
| | | 47.8 | Yes |
| Medline Purple | MDS 148055 | 58.2 | Yes |
| | | 55.8 | Yes |
| | | 60.6 | Yes |

Prior art examples, listed in Table 1, were purchased and three replicates of each were evaluated with this method. All prior art samples had blood on the back of the product after testing.

TABLE 2

Window Design Invention Examples

| Prototype Number | Core Basis Weight (gsm) | Wrapped Core Thickness (inches) | % Fluid Contained | Fluid present on bottom outward facing side of product? |
|---|---|---|---|---|
| 1 | 634 | 0.41 | 88 | No |
| 2 | 870 | 0.42 | 73.8 | No |
| 3 | 1068 | 0.79 | 100 | No |
| 4 | 611 | 0.51 | 100 | No |
| 5 | 896 | 0.52 | 100 | No |
| 6 | 1082 | 0.52 | 100 | No |
| 7 | 649 | 0.48 | 100 | No |
| 8 | 832 | 0.73 | 100 | No |
| 9 | 1062 | 0.57 | 100 | No |
| 10 | 637 | 0.59 | 100 | No |
| 11 | 827 | 0.69 | 100 | No |
| 12 | 1125 | 0.71 | 100 | No |

Table 2 shows the results for the testing of the window design invention examples. Prototypes vary by core basis and thickness (shown in table). In most of the prototypes there was 100% fluid containment. Two samples with a lower core thickness contained most of the fluid, but not all. All of the fluid was contained on samples with a core thickness of at least 0.48 inches. None of the prototypes had fluid present on the bottom outward facing side of the pack.

TABLE 3

Embossed channel design fluid containment results.

| Prototype Number | Core Basis Weight (gsm) | Thickness (inches) | % Fluid Contained | Fluid present on bottom outward facing side of product |
|---|---|---|---|---|
| E1 | 975 gsm | 0.57 | 97.6 | No |

Table 3 shows the results for the fluid containment testing of the embossed channel design. Prototype E1 was tested and showed 97.6% fluid containment and no fluid present on the bottom outward facing side of the pack.

TABLE 4

Fluid containment results for folded over designs.

| Prototype Number | Core Single Thickness Basis Weight (gsm) | Single layer of airlaid core thickness (inches) | % Fluid Contained | Fluid present on bottom outward facing side of product |
|---|---|---|---|---|
| A1 | 210 | 0.25 | 100 | No |
| A2 | 300 | 0.13 | 85.6 | No |
| A3 | 210 | 0.25 | 100 | No |
| A4 | 300 | 0.13 | 90.4 | No |

Table 4 shows the fluid containment results for folded over design prototypes. Prototypes A1-A4 differ in core single thickness basis weight (gsm) and single layer of airlaid core thickness (inches). The lower core single thickness basis weight and the lower single layer of airlaid core thickness prototypes (A1 and A3) performed better with 100% fluid containment. All of the prototypes did not have any fluid present on the bottom outward facing side of the pack.

Unlike the embodiments of the current invention, prior art products do not maximize fluid containment. Prior art products are designed with a thermal pack which sits on top of an absorbent core, all of which is overlaid by a nonwoven layer. This design creates a slanted surface down which lochia fluid flows, rather than capturing the fluid in the pad. Since the top nonwoven layer is not in contact with the absorbent core, the fluid is not wicked through the nonwoven into the core. The combination of shape and lack of absorbency results in a product which does not contain fluid. Instead, the prior art is viewed solely as cold therapy, and is often used in combination with a separate absorbent pad.

In a preferred embodiment (FIG. 1), a perineal thermal pack [10] consists of a thermal pouch [23] attached to a pad [12]. The pad [12] is formed of an absorbent core [27] with a top sheet [19] and bottom sheet (20) to hold the absorbent core [27] in place. The pad can also be comprised of an absorbent core and top sheet without a bottom sheet. It is preferential to have a bottom sheet. Having the bottom nonwoven sheet pulls down on the top nonwoven sheet where they are glued together in the void, and this helps to form deeper liquid pooling areas around the perimeter of the center void. Also, having two layers of nonwoven helps with liquid aqusition. The bottom sheet can act like an aqusition/distribution layer. The absorbent core can be fluff pulp. The absorbent core can have a center void area. Both the top sheet [19] and the back sheet [20] can be nonwovens. The nonwoven sheets can be attached to each other at the area of the voided core. The nonwoven sheets can be attached to the pouch in this area. The perineal thermal pack has a bottom film layer [30] and optionally a bottom nonwoven layer [21]. The perineal thermal pack [10] may have an adhesive strip [24] running down the center of the pad the long way with a release liner [25]. In a preferred embodiment, the thermal pouch is embedded in the pad [12].

Figure 2:
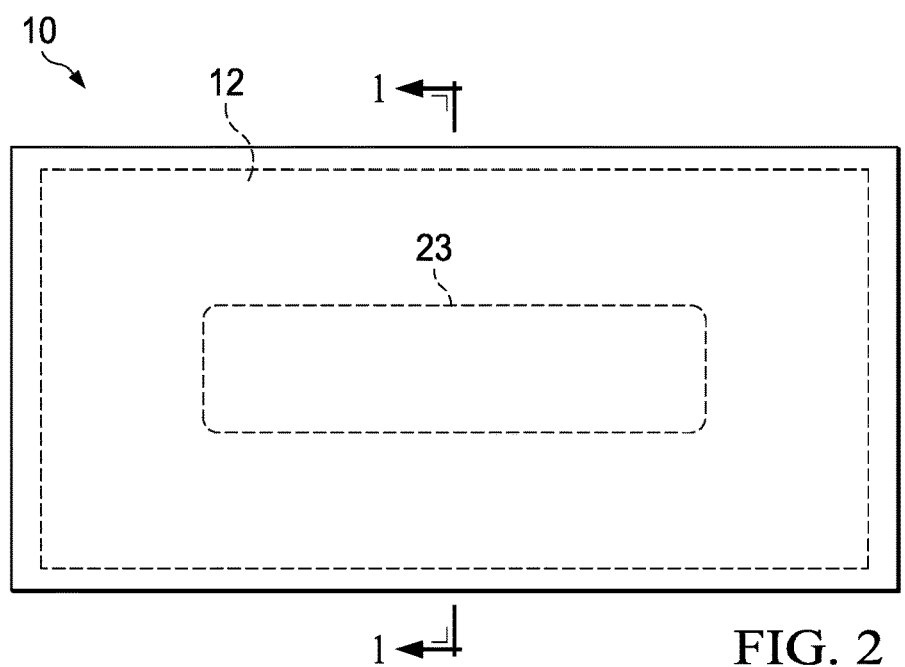
FIG. 2 is a top view of the embodiment of FIG. 1.
Figure 3:
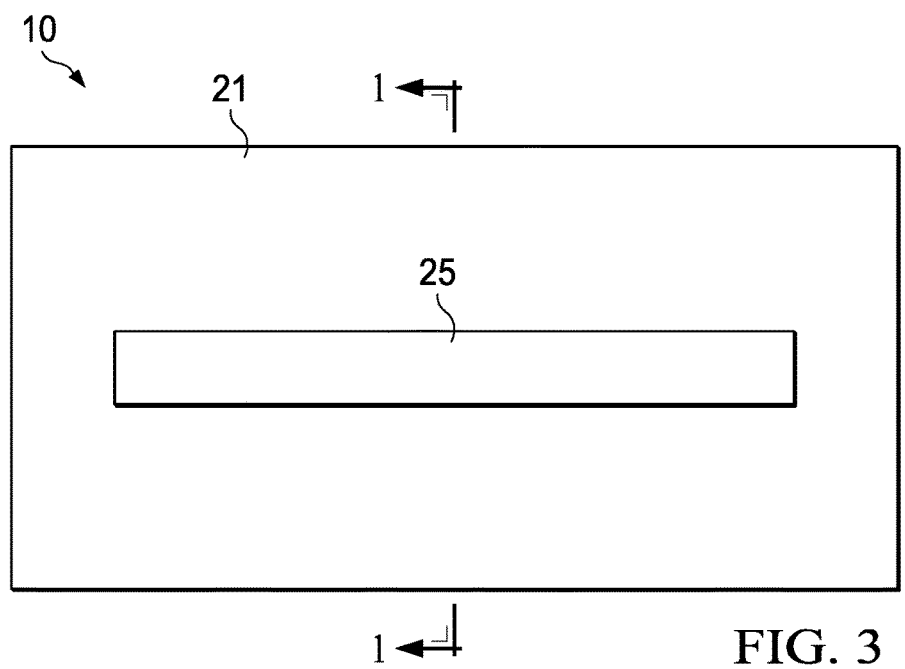
FIG. 3 is a bottom view of the embodiment of FIG. 1.

FIG. 2 shows the top view and FIG. 3 shows the bottom view of the preferred embodiment of FIG. 1.

Figure 4:
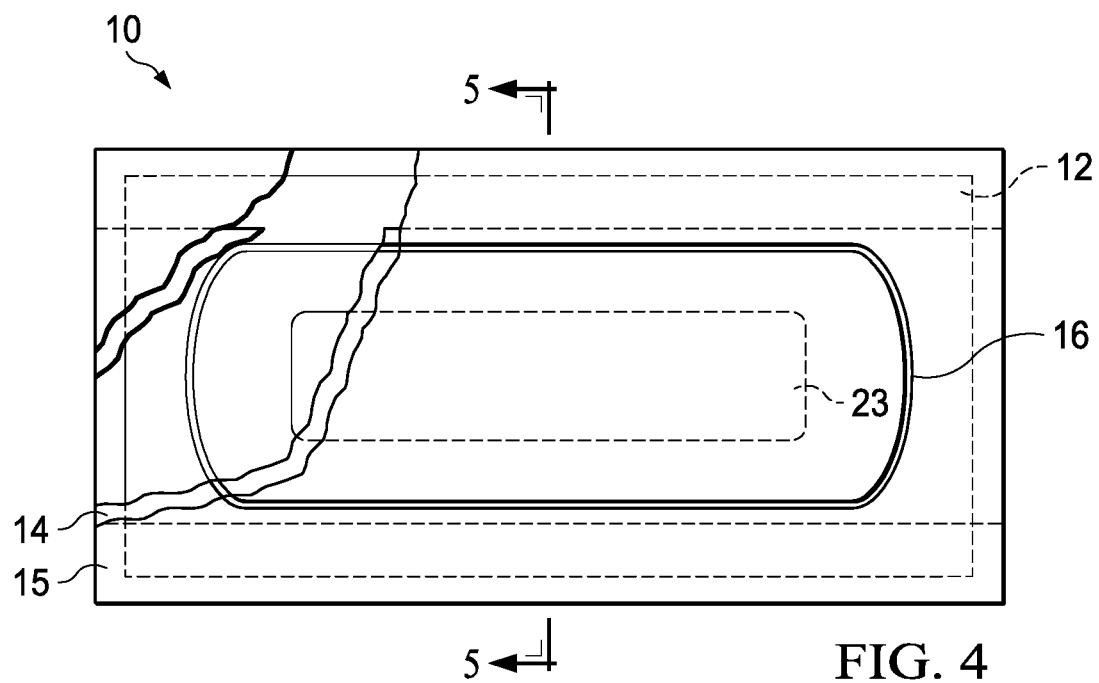
FIG. 4 is a top view of another exemplary embodiment of the current application.
Figure 5:
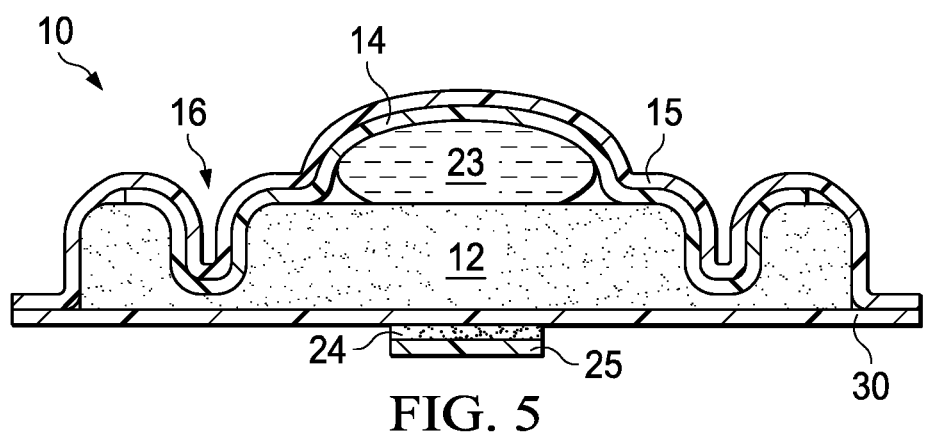
FIG. 5 is a cross-section view of the embodiment of FIG. 4.

Another embodiment (FIGS. 4 and 5) of the perineal thermal pack [10] consists of a thermal pouch [23] attached to a pad [12] that can comprise an absorbent core and surrounding nonwoven sheets (19 and 20 in FIG. 1). The pad [12] can optionally be an absorbent core and a top sheet [19] without a bottom sheet. Top sheet [19] is not shown in the drawing, but is present in the pad [12]. Above the pad [12] and thermal pouch [23] there are one or more absorbent nonwoven layers, referred to as the overwrap. In one embodiment, there is an acquisition distribution layer [14] below an absorbent nonwoven material cover sheet [15]. In other embodiments, the overwrap is only the top cover sheet [15]. There are grooves or channels [16] embossed into the nonwoven cover sheet [15], acquisition distribution layer [14], and pad [12] between the edge of the pad [12] and the thermal pouch [23] in any pattern. The grooves [16] shown in the figure are continuous and can follow the shape of the pad [12] or have a different shape. In the particular embodiment of FIG. 4, the grooves do not match the overall shape of the pad. Optionally cross grooves can be formed across the pad core where the cold pouch is connecting with the longitudinal channels. These cross channels help to direct the fluid into the core underneath the cold pouch, increasing the fluid hold capacity of the pad. The embodiment of FIG. 5 also includes a bottom backing layer. Preferably this comprises a film layer [30]. The backing layer can also include a nonwoven layer [21], as shown in FIG. 1, underneath the film layer [30]. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including the edge and right outside the perimeter of the cold pouch.

Figure 6:
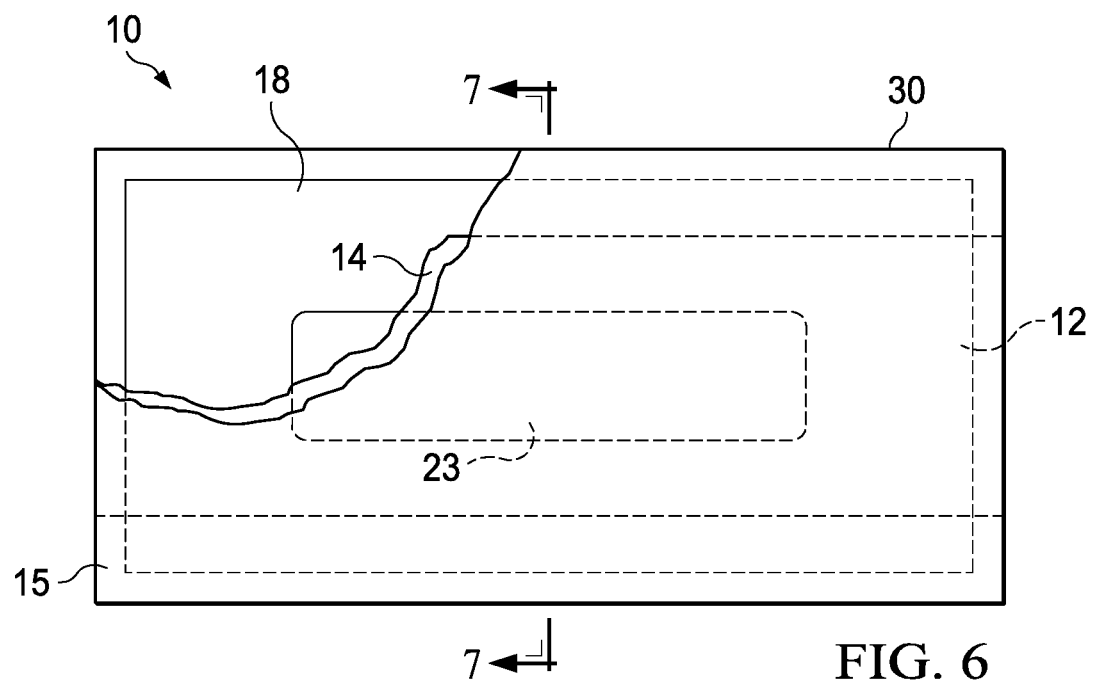
FIG. 6 is a top view of another exemplary embodiment of the current application.
Figure 7:
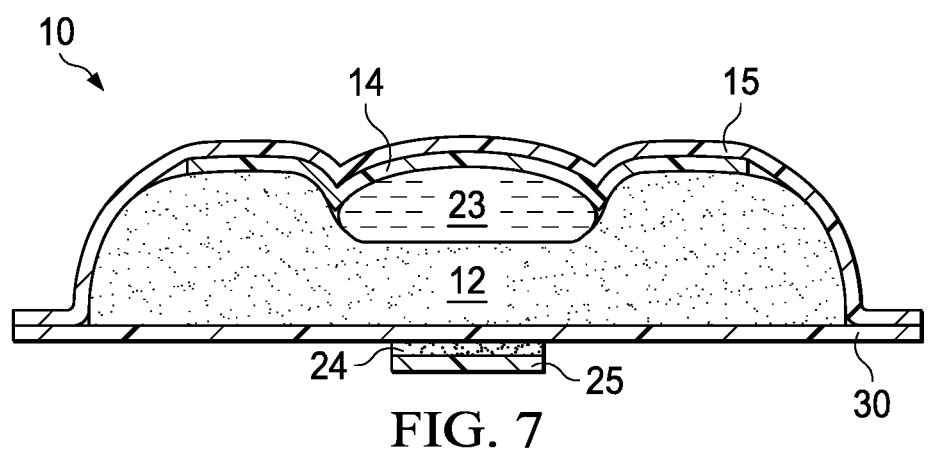
FIG. 7 is a cross section of the embodiment of FIG. 6.

In one embodiment (FIGS. 6 and 7) of the perineal thermal pack [10], a thermal pouch [23] is attached to a pad [12] that can comprise an absorbent core and surrounding top and bottom sheets (19 and 20 in FIG. 1). The pad can optionally be an absorbent core and a top sheet [19] without a bottom sheet. Top sheet [19] is not shown in the drawing, but is present in the pad [12]. The pad's [12] absorbent core is thinner where the thermal pouch [23] is attached. The thinner section under the thermal pouch can be achieved by compressing the core, or alternatively the core can be formed with less absorbent core material. There is an overwrap above the pouch and pad. In this embodiment, there is an acquisition distribution layer [14] below an absorbent nonwoven material top sheet [15]. The overwrap may consist of both these layers or just one. The top sheet [15] can extend to the backing layer which comprises at least film layer [30]. Backing layer can also comprise an additional nonwoven layer [21] below [30]. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including the edge and right outside the perimeter of the cold pouch. The overwrap can also be fully attached to the pad in all areas but that of the cold pouch.

Figure 8:
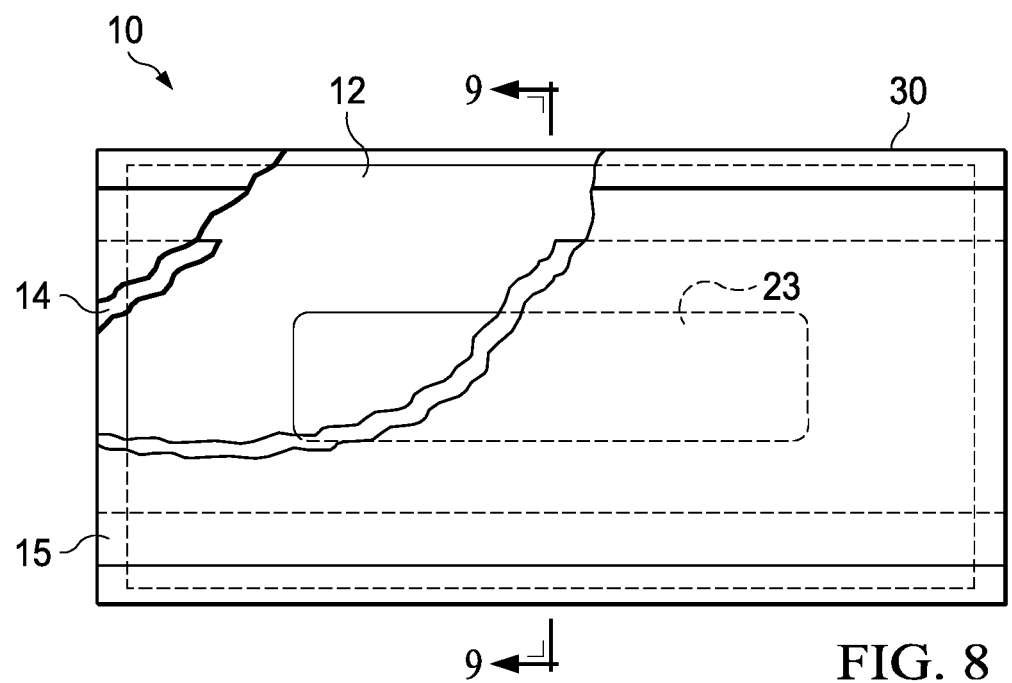
FIG. 8 is a top view of another exemplary embodiment of the current application.
Figure 9:
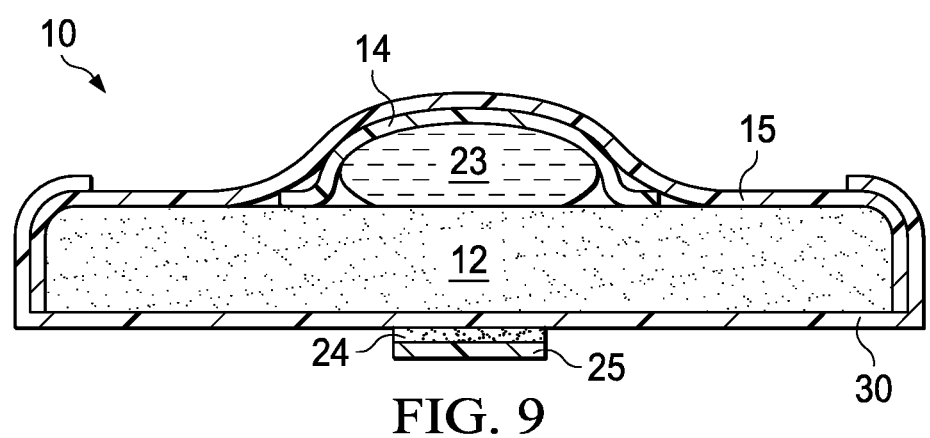
FIG. 9 is a cross section of the embodiment of FIG. 8.

Another embodiment (FIGS. 8 and 9) of the perineal thermal pack [10] consists of a thermal pouch [23] attached to a pad [12] that can comprise an absorbent core and surrounding nonwoven sheets (19 and 20 in FIG. 1). The pad can optionally be an absorbent core and a top sheet [19] without a bottom sheet. Top sheet [19] is not shown in the drawing, but is present in the pad [12]. The long side of the pad film border [30] is folded up to act as a guard to contain fluid. The pad [12] can be thinner where the thermal pouch [23] is attached. Above the pad [12] and attached thermal pouch [23], there is an acquisition distribution layer [14] and above the acquisition distribution layer [14], there is an absorbent nonwoven material top sheet [15]. On the long edges of the pad [12], the nonwoven material top sheet [15] is attached to the film edge border [30] of the pad [12] such that the film edges of the pad fold up. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including right outside the perimeter of the cold pouch. The overwrap can also be fully attached to the pad in all areas but that of the cold pouch.

Figure 10:
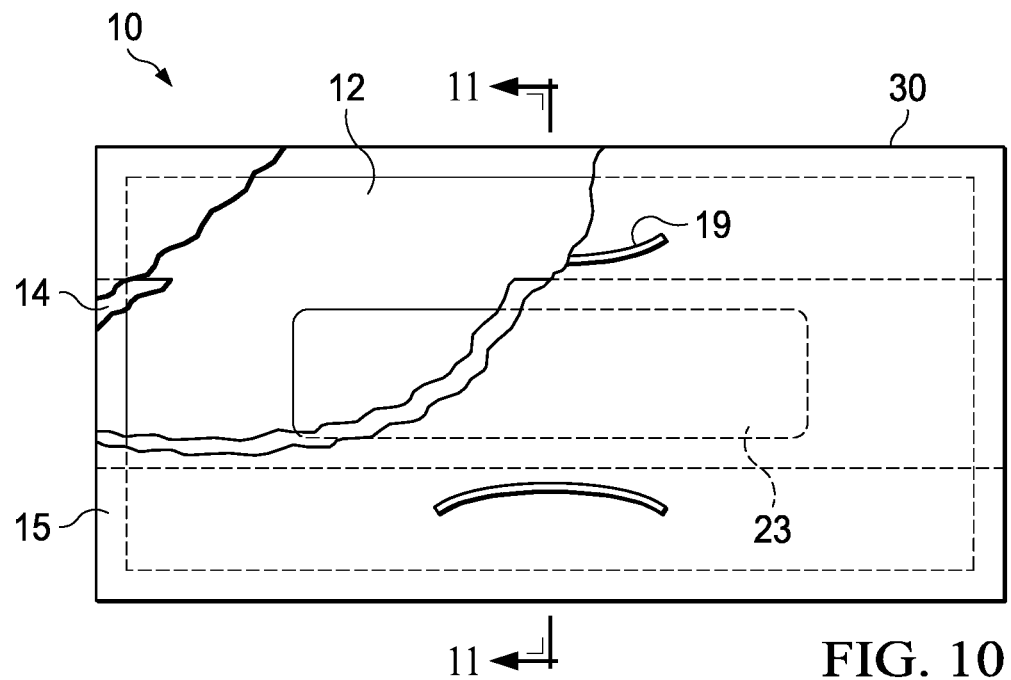
FIG. 10 is top view of an embodiment of the current application.
Figure 11:
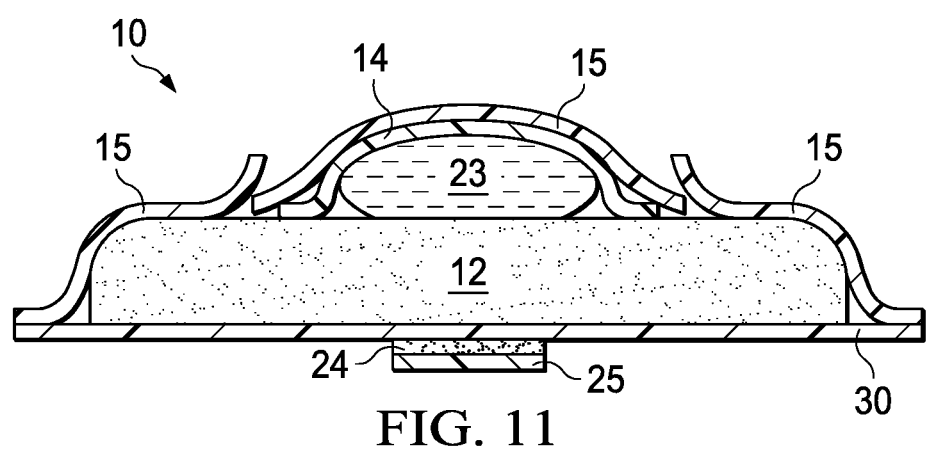
FIG. 11 is a cross-section view of the embodiment of FIG. 10.

Yet another embodiment (FIGS. 10 and 11) of the perineal thermal pack [10] consists of a thermal pouch [23] attached to a pad [12] that can comprise an absorbent core and surrounding nonwoven sheets (19 and 20 in FIG. 1). The pad can optionally be an absorbent core and a top sheet [19] without a bottom sheet. The pad core [27] can be thinner where the thermal pouch [23] is attached. The one or more absorbent layers have a slit [19] cut into them such that fluid can flow from the center of the perineal cold pack [10] toward the edges and fall into the slit [19]. In a preferred embodiment, there is an acquisition distribution layer [14] below an absorbent nonwoven top sheet [15] and there are slits [19] in the top layer on both sides of the cold pouch that have a curved shape. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including right outside the perimeter of the cold pouch. The overwrap can also be fully attached to the pad in all areas but that of the cold pouch.

Figure 12:
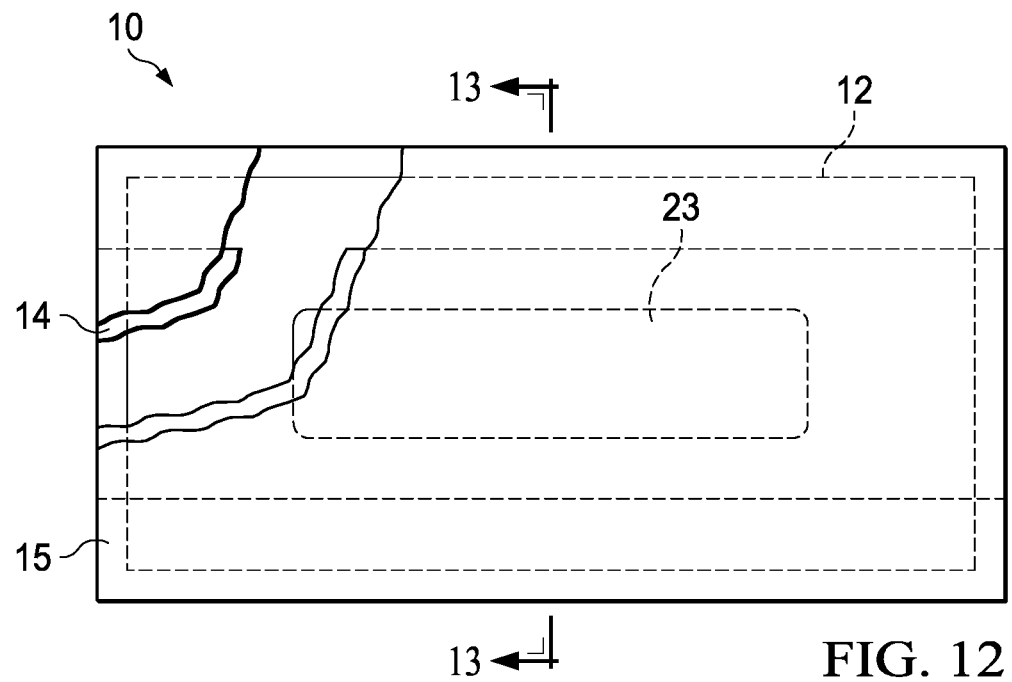
FIG. 12 is a top view of an embodiment of the current application.
Figure 13:
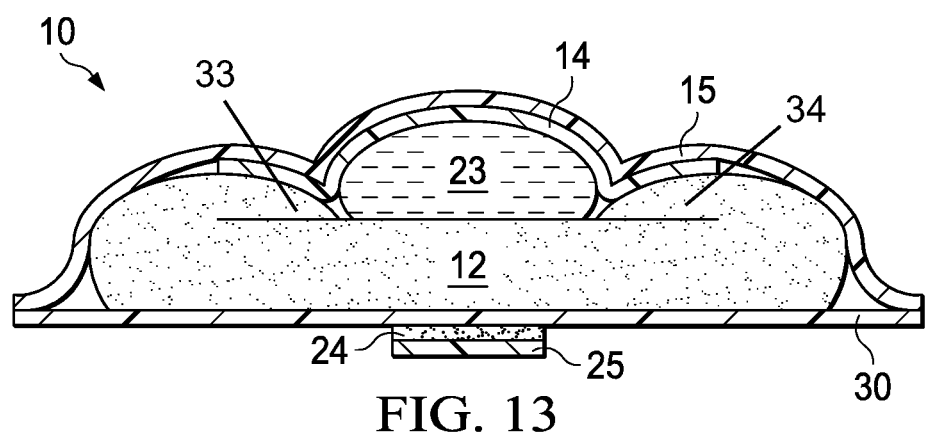
FIG. 13 is a cross-section view of the embodiment of FIG. 12.

In one embodiment (FIGS. 12 and 13) of the perineal thermal pack [10], a thermal pouch [23] is attached to a pad [12] that can comprise an absorbent core and surrounding nonwoven sheets (19 and 20 in FIG. 1). The pad can optionally be an absorbent core and a top sheet [19] without a bottom sheet. The pad [12] is compressed or thinner where the thermal pouch [23] is attached. The pad [12] core is folded over at a first edge 1331 and a second edge 1341 to form a single thickness under the thermal pouch and a double thickness at the edges of the core where it is folded over. The overwrap comprises an acquisition distribution layer [14] and nonwoven material top sheet [15]. The absorbent core [27] or fluff pulp, is folded over. The nonwoven top sheet [15] extends to the end of the film [30]. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including right outside the perimeter of the cold pouch. The overwrap can also be fully attached to the pad in all areas but that of the cold pouch.

Figure 14:
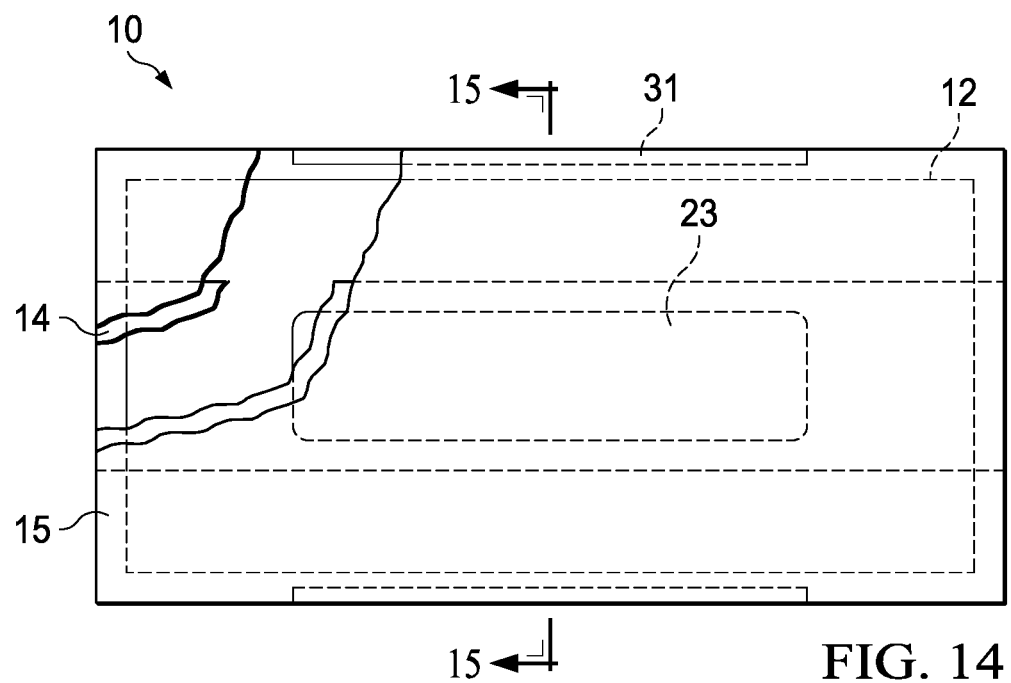
FIG. 14 is a top view of an exemplary embodiment of the current application.
Figure 15:
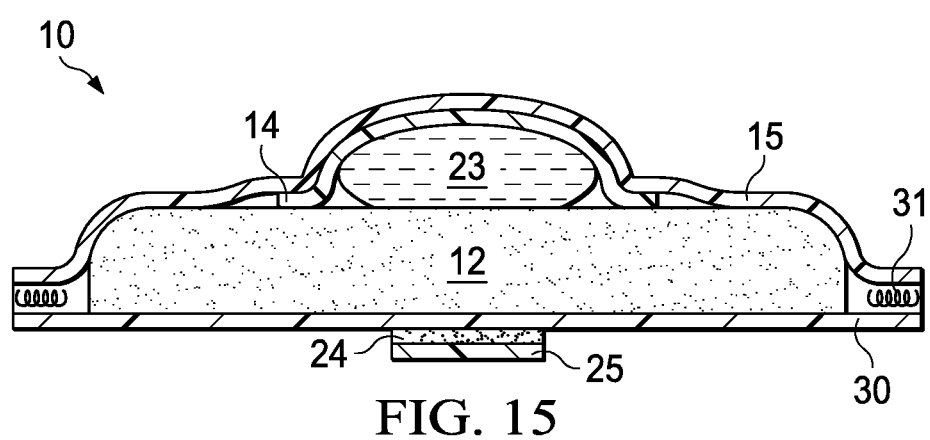
FIG. 15 is a cross-section view of the embodiment of FIG. 14.

In another embodiment (FIGS. 14 and 15) a perineal thermal pack [10] is comprised of a thermal pouch [23] and pad [12] that can comprise an absorbent core and surrounding nonwoven sheets (19 and 20 in FIG. 1). The pad can optionally be an absorbent core and a top sheet [19] without a bottom sheet. The embodiment further comprises elastic strips 31. The elastic strips pull down the length of the pad on the edges of the pad from the leg cuffs, for fluid containment. The overwrap comprises an acquisition distribution layer [14] and nonwoven material top sheet [15]. The nonwoven top sheet [15] extends to the end of the pad. The ADL [14] only partially extends. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including right outside the perimeter of the cold pouch. The overwrap can also be fully attached to the pad in all areas but that of the cold pouch.

Figure 16:
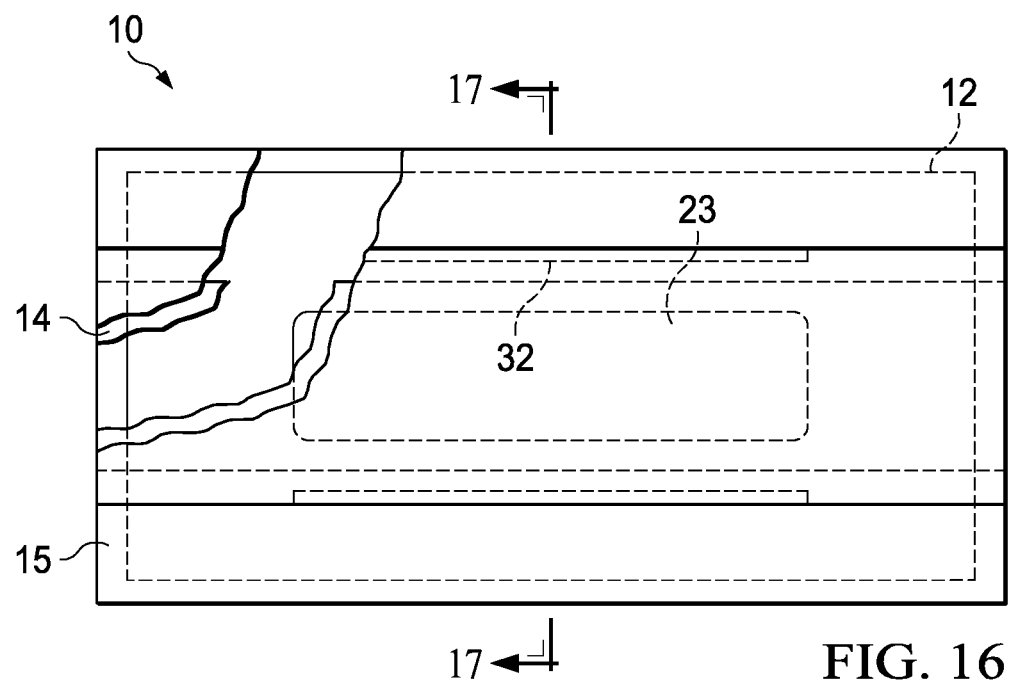
FIG. 16 is a top view of an embodiment of the current application.
Figure 17:
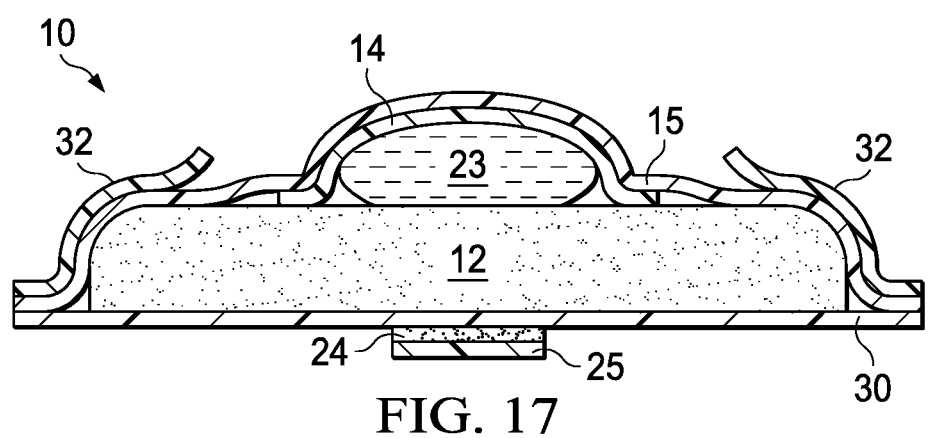
FIG. 17 is a cross-section view of the embodiment of FIG. 16.

In another embodiment (FIGS. 16 and 17) a perineal thermal pack [10] is comprised of a thermal pouch [23] and a pad [12] that can comprise an absorbent core and surrounding nonwoven sheets (19 and 20 in FIG. 1). The pad can optionally be an absorbent core and a top sheet [19] without a bottom sheet. The embodiment further comprises elastic leg cuffs [32]. The overwrap comprises an acquisition distribution layer [14] and nonwoven material top sheet [15]. The nonwoven top sheet [15] extends to the end of the pad. The optional ADL [14] only partially extends. The elastic leg cuff [32] extends over the nonwoven top sheet [15]. Attached to the backing layer can also optionally be an adhesive layer [24] and release liner [25]. Additional adhesive layers are not shown, but can be present. Layers [14] and [15] can be joined by an adhesive layer. The pouch [23] can be attached to the pad [12] by an adhesive layer. Overwrap layers [14] and [15] can be joined to the pad [12] and film [30] with an adhesive. Overwrap layers [14] and [15] are attached the pad at multiple points, including right outside the perimeter of the cold pouch. The overwrap can also be fully attached to the pad in all areas but that of the cold pouch.

The foregoing description is provided to enable any person skilled in the art to practice the various example implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

The invention claimed is:

1. A device for applying thermal therapy to a perineal area of a patient, comprising:
 a pad comprising:
  an absorbent core having a void, and
  a top sheet and a bottom sheet, the top and bottom sheets surrounding the absorbent core;
 a backing layer; and
 a thermal pouch underlying the top and bottom sheets,
 wherein the absorbent core forms a perimeter of the void,
 wherein the top sheet is attached to the bottom sheet at the void, and
 wherein the entire thermal pouch is nested within the void.

2. The device of claim 1, wherein at least one of the top and bottom sheets is liquid permeable.

3. The device of claim 1, wherein at least one of the top and bottom sheets is nonwoven.

4. The device of claim 2, wherein the top sheet and bottom sheet are liquid permeable.

5. The device of claim 3, wherein the top sheet and the bottom sheet are nonwoven.

6. The device of claim 1, wherein the backing layer is not liquid-permeable.

7. The device of claim 6, wherein the backing layer is a film.

8. The device of claim 1, wherein the absorbent core comprises at least one of fluff pulp and super absorbent polymer.

9. The device of claim 1, wherein the void is in the center of the pad.

10. The device of claim 1, wherein the top and bottom sheets are fully connected to the absorbent core except for in the void.

11. The device of claim 1, wherein the thermal pouch substantially fills the void in the pad.

12. The device of claim 1, wherein the backing layer comprises a film layer and a nonwoven layer, wherein the backing layer is adjacent the pad.

13. The device of claim 1, further comprising an adhesive layer and release liner beneath the backing layer.

14. The device of claim 1, wherein the thermal pouch is not removable.

15. The device of claim 1, wherein the thermal pouch is for cold therapy.

16. The device of claim 1, wherein the core is at least 0.48 inches in thickness.

17. The device of claim 1, wherein the device contained greater than about 90% of the liquid released in a fluid containment test.

18. The device of claim 17, wherein the device did not have any fluid present on a bottom outward facing side of the device in the fluid containment test.

19. A device for applying thermal therapy to a perineal area of a patient, comprising:
   a pad comprising an absorbent core with a center void;
   top and bottom nonwoven sheets, wherein the top and bottom nonwoven sheets are connected at the center void;
   a thermal pouch nested in the center void, underlying the top and bottom nonwoven sheets, wherein the entire thermal pouch is nested in the center void; and
   a backing layer,
   wherein the absorbent core forms a perimeter of the center void.

20. A process for making a device for providing thermal therapy to a perineal area of a patient comprising:
   forming an absorbent core that includes a voided area without absorbent core, wherein the absorbent core forms a perimeter of the voided area;
   wrapping the core in a top sheet and bottom sheet;
   securing the top and bottom sheets to the absorbent core;
   attaching the top sheet to the bottom sheet at the voided area;
   providing a thermal pouch that underlays the top and bottom sheets, wherein the entire thermal pouch is nested in the voided area without the absorbent core; and
   adhering a backing layer to a bottom of the thermal pouch and the wrapped absorbent core.

21. The process of claim 20, wherein the forming an absorbent core with a voided area comprises forming a core and removing a portion to create the voided area.

* * * * *